(12) United States Patent
Lech et al.

(10) Patent No.: US 11,949,297 B2
(45) Date of Patent: Apr. 2, 2024

(54) METHODS FOR ANALOG TEMPERATURE COMPENSATION OF BIAS AND OFFSETS OF A DIFFERENTIAL SENSOR

(71) Applicant: Covidien LP, Mansfield, MA (US)

(72) Inventors: Richard S. Lech, Hamden, CT (US); Alok Agrawal, North Haven, CT (US)

(73) Assignee: COVIDIEN LP, Mansfield, MA (US)

( * ) Notice: Subject to any disclaimer, the term of this patent is extended or adjusted under 35 U.S.C. 154(b) by 296 days.

(21) Appl. No.: 17/431,463

(22) PCT Filed: Mar. 2, 2020

(86) PCT No.: PCT/US2020/020695
§ 371 (c)(1),
(2) Date: Aug. 17, 2021

(87) PCT Pub. No.: WO2020/185440
PCT Pub. Date: Sep. 17, 2020

(65) Prior Publication Data
US 2022/0140702 A1   May 5, 2022

Related U.S. Application Data

(60) Provisional application No. 62/815,513, filed on Mar. 8, 2019.

(51) Int. Cl.
*H02K 11/24* (2016.01)
*A61B 34/00* (2016.01)
(Continued)

(52) U.S. Cl.
CPC .............. *H02K 11/24* (2016.01); *A61B 34/25* (2016.02); *A61B 34/37* (2016.02); *A61B 34/74* (2016.02);
(Continued)

(58) Field of Classification Search
CPC .......... H02K 11/24; H02K 11/25; H02K 5/00; H02K 16/00; A61B 34/25; A61B 34/37;
(Continued)

(56) References Cited

U.S. PATENT DOCUMENTS

| 5,048,343 | A  | 9/1991 | Oboodi et al. |
| 6,265,857 | B1 | 7/2001 | Demsky et al. |

(Continued)

FOREIGN PATENT DOCUMENTS

| CN | 1969237 A | 5/2007 |
| CN | 101103260 A | 1/2008 |

(Continued)

OTHER PUBLICATIONS

Supplementary Partial European Search Report dated May 8, 2023 for European Patent Application No. 20769261.7 (13 Pages).

(Continued)

*Primary Examiner* — David Luo
(74) *Attorney, Agent, or Firm* — Carter, DeLuca & Farrell, LLP

(57) ABSTRACT

A measurement circuit that is configured to provide a torque reading to a motion controller includes an offset controller and an amplifier. The offset controller is configured to read a temperature signal and to generate an offset voltage in response to receiving the temperature signal. The amplifier is configured to read a differential voltage from a differential sensor and to receive the offset voltage from the offset controller. The amplifier is also configured to add the offset voltage to the differential voltage after applying a gain to the differential voltage to generate an adjusted voltage. The amplifier is then configured to transmit the adjusted voltage.

16 Claims, 7 Drawing Sheets

(51) Int. Cl.
*A61B 34/37* (2016.01)
*A61B 90/00* (2016.01)
*G01K 1/02* (2021.01)
*G01K 7/00* (2006.01)
*G01L 3/10* (2006.01)
*G01L 25/00* (2006.01)
*H02K 11/25* (2016.01)
*H02P 29/68* (2016.01)

(52) U.S. Cl.
CPC .............. *G01K 1/026* (2013.01); *G01K 7/00* (2013.01); *G01L 3/108* (2013.01); *G01L 25/003* (2013.01); *H02K 11/25* (2016.01); *H02P 29/68* (2016.02); *A61B 2090/066* (2016.02)

(58) Field of Classification Search
CPC .............. A61B 34/74; A61B 2090/066; A61B 2090/036; A61B 2090/0811; A61B 2090/371; A61B 90/361; A61B 34/30; A61B 2017/00084; A61B 2017/00725; G01K 1/026; G01K 7/00; G01K 13/00; G01L 3/108; G01L 25/003; H02P 29/68
USPC .................................. 318/445, 634, 632, 560
See application file for complete search history.

(56) References Cited

U.S. PATENT DOCUMENTS

| | | | | |
|---|---|---|---|---|
| 6,380,706 | B1 * | 4/2002 | Kifuku | B62D 5/0463 |
| | | | | 318/434 |
| 6,622,576 | B1 | 9/2003 | Nakano et al. | |
| 7,038,530 | B2 * | 5/2006 | Chou | G05F 3/247 |
| | | | | 327/543 |
| 7,044,264 | B2 * | 5/2006 | Uryu | B62D 5/0481 |
| | | | | 701/42 |
| 8,828,023 | B2 | 9/2014 | Neff et al. | |
| 10,498,269 | B2 * | 12/2019 | Zemlok | H02P 7/29 |
| 2003/0029251 | A1 | 2/2003 | Ueno | |
| 2005/0237104 | A1 | 10/2005 | Chou | |
| 2010/0321096 | A1 | 12/2010 | Sudjian | |
| 2018/0153634 | A1 | 6/2018 | Zemlok et al. | |

FOREIGN PATENT DOCUMENTS

| | | |
|---|---|---|
| CN | 102395867 A | 3/2012 |
| CN | 106233214 A | 12/2016 |
| CN | 107743384 A | 2/2018 |
| EP | 0984256 A2 | 3/2000 |

OTHER PUBLICATIONS

International Search Report dated Jun. 17, 2020 and Written Opinion completed Jun. 16, 2020 corresponding to counterpart Int'l Patent Application PCT/US2020/020695.

Chinese Office Action issued in corresponding Chinese Application No. 202080012450.6 dated Apr. 15, 2023, 24 pages.

Extended European Search Report dated Sep. 20, 2023 for European Patent Application No. 20769261.7 (13 pages).

* cited by examiner

US 11,949,297 B2

METHODS FOR ANALOG TEMPERATURE COMPENSATION OF BIAS AND OFFSETS OF A DIFFERENTIAL SENSOR

CROSS-REFERENCE TO RELATED APPLICATIONS

The present application is a U.S. National Stage Application filed under 35 U.S.C. § 371(a) claiming the benefit of and priority to International Patent Application No. PCT/US20/20695, filed Mar. 2, 2020, which claims the benefit of and priority to U.S. Provisional Patent Application Ser. No. 62/815,513, filed Mar. 8, 2019, the entire disclosures of each of which being incorporated by reference herein.

FIELD OF THE INVENTION

The present invention relates to robotic surgical systems used in minimally invasive medical procedures because of their increased accuracy and expediency relative to handheld surgical instruments.

BACKGROUND

Robotic surgical systems have been used in minimally invasive medical procedures. During such a medical procedure, the robotic surgical system is controlled by a surgeon interfacing with a user interface. The user interface allows the surgeon to manipulate an end effector that acts on a patient. The user interface includes an input controller or handle that is moveable by the surgeon to control the robotic surgical system.

The end effectors of the robotic surgical system are positioned at the end of robotic arms. Each end effector is manipulated by an instrument drive unit (IDU). The IDU includes a drive motor that is associated with the end effector to move the end effector about a respective axis or to perform a particular function of the end effector (e.g., approximate, pivot, etc. jaws of the end effector). The IDU can include a plurality of drive motors with each drive motor being associated with a respective degree of freedom or function of the end effector.

Each drive motor of the IDU can be associated with the respective degree or degrees of freedom of the end effector by a drive mechanism (e.g., a drive cable, a drive rod and/or a drive screw). The position or pose of the end effector is controlled by the position of the drive motors. The load on each of the drive motors due to a given pose or a desired end effector motion can be determined by a torque sensor associated with each motor of the IDU. It is known that readings from torque sensors may vary as temperature varies. These variations may also affect calibration of torque sensors of the IDU.

There is a continuing need to compensate for temperature fluctuations of torque sensors. In addition, there is a continuing need for precisely and accurately calibrating torque sensors of an IDU.

SUMMARY

This disclosure relates generally to measurement circuits for a strain gauge that correct for temperature dependent and temperature independent fluctuations of the strain gauge such that a torque signal provided by the measurement circuit is adjusted or corrected such that a motion controller receiving the torque signal is not required to correct for the temperature dependent and temperature independent factors affecting the strain gauge.

Additionally, this disclosure is for the continuous update of an analog offset of the zero point, where the offset may be applied even while under load, but determined during calibration under zero load. Also, this disclosure is for the continuous update of the offset voltage during operation, not only during calibration.

In an aspect of the present disclosure, a measurement circuit that is configured to provide a torque reading to a motion controller includes an offset controller and an amplifier. The offset controller is configured to read a temperature signal and to generate an offset voltage in response to reading the temperature signal. The amplifier is configured to receive a differential voltage from a differential sensor and to receive the offset voltage from the offset controller. The amplifier is also configured to add the offset voltage to the differential voltage after applying a gain to the differential voltage to generate an adjusted voltage. The amplifier is then configured to transmit the adjusted voltage.

In aspects, the measurement circuit includes a temperature sensor that is configured to transmit the temperature signal indicative of a temperature of the differential sensor. The temperature sensor may be configured to output the temperature signal as a digital temperature signal and the offset controller may be a digital-to-analog converter that is configured to convert the digital temperature signal to an analog voltage offset indicative of a temperature of the differential sensor.

In some aspects, the measurement circuit includes a differential sensor that is configured to generate the differential voltage which is indicative of a torque of a motor and to transmit the differential voltage to the amplifier. The offset controller may be configured to generate the offset voltage which includes a first component that corrects for manufacturing tolerances of the differential sensor and a second component that corrects for temperature drift of the differential sensor.

In certain aspects, the differential sensor is a strain gauge.

In certain aspects of the present disclosure, the measurement circuit includes an analog-to-digital converter that is configured to receive the adjusted voltage from the amplifier, to convert the adjusted voltage to a digital torque signal indicative of the adjusted voltage which is corrected for temperature drift, and to transmit the torque signal.

In another embodiment of the present disclosure, an instrument drive unit is configured to control a tool of a surgical instrument and includes a first motor, a first torque transducer, and a motion controller. The first torque transducer includes a first torque measurement circuit that is configured to determine a torque of the first motor. The first torque measurement circuit includes an offset controller and an amplifier. The offset controller is configured to read a first temperature signal and to generate an offset voltage in response to reading the first temperature signal. The amplifier is configured to read a differential voltage from a differential sensor, to receive the offset voltage from the offset controller, to add the offset voltage to the differential voltage after applying a gain to the differential voltage to generate an adjusted voltage, and to transmit the adjusted voltage. The motion controller is configured to receive a first torque signal from the first measurement circuit indicative of the adjusted voltage and to control the first motor in response to the first torque signal.

In aspects, the first torque measurement circuit includes an analog-to-digital converter that is configured to receive the adjusted voltage from the amplifier and to transmit the first torque signal to the motion controller.

In some aspects, the instrument drive unit includes a second motor and a second torque transducer. The second torque transducer may include a second torque measurement circuit that is configured to determine a torque of the second motor. The motion controller is configured to receive a second torque signal from the second measurement circuit that is indicative of the torque of the second motor which is adjusted for a temperature drift of the second torque transducer. The first measurement circuit may include a first temperature sensor that is configured to transmit the first temperature signal indicative of a temperature of the first torque transducer to the offset controller and the second measurement circuit may include a second temperature sensor that is configured to transmit the second temperature signal indicative of a temperature of the second torque transducer to the offset controller. Alternatively, the first measurement circuit may include a temperature sensor that is configured to transmit the first temperature signal indicative of a temperature of the first torque transducer to the offset controller and to transmit the second temperature signal indicative of a temperature of the second torque transducer to the offset controller.

In another aspect of the present disclosure, a method of calibrating a measurement circuit of a differential sensor includes setting a gain constant for the measurement circuit, determining a bias voltage function of the measurement circuit to compensate for manufacturing tolerances and temperature drift of the differential sensor, and programming the bias voltage into an offset controller of the measurement circuit. Determining the bias voltage function may include determining a first component of the bias voltage function of the measurement circuit that is independent of a temperature of the differential sensor, determining a temperature dependent function for a second component of the bias voltage function, and generating the bias voltage function from the first and second components. The offset controller is configured to receive a temperature signal from a temperature sensor and to generate a bias voltage from the bias voltage function in response to receiving the temperature signal.

In aspects, determining the first component of the bias function includes setting the differential sensor in a no load condition, determining a temperature of the differential sensor, calculating the second component based on the temperature of the differential sensor, adjusting the bias voltage of the offset controller of the measurement circuit to the calculated second component, reading an output voltage of the measurement circuit when the bias voltage is set to the calculated second component, and determining the first component as the difference between a predetermined midrange value and the output voltage of the measurement circuit.

In some aspects, determining the second component of the bias voltage function includes, setting the differential sensor in a no load condition, adjusting the bias voltage of the offset controller to the first component of the bias voltage function, reading an output voltage of the measurement circuit and a temperature of the differential sensor at which the output voltage was taken for a plurality of temperatures of the differential sensor in the no load condition, and determining the temperature based function for the second component based on the recorded output voltages.

In certain aspects, setting the gain constant for the measurement circuit occurs after programming the bias voltage function. Setting the gain constant for the measurement circuit may include applying a known positive torque to the differential sensor and recording a positive output voltage in response to applying the known positive torque, applying a known negative torque to the differential sensor and recording a negative output voltage in response to applying the known negative torque, and determining the gain constant of the measurement circuit from a ratio of the known positive and negative torques and the recorded positive and negative output voltages. Setting the gain constant for the measurement circuit may include setting the differential sensor in a no load condition and adjusting the bias voltage such that an adjusted voltage of the measurement circuit is a predetermined midrange value before applying the known positive and negative torques.

In particular aspects, the method may include detecting a no load condition of the differential sensor and updating the bias voltage function based on an output voltage of the measurement circuit and a temperature of the differential sensor when the no load condition is detected.

Further, to the extent consistent, any of the aspects described herein may be used in conjunction with any or all of the other aspects described herein.

BRIEF DESCRIPTION OF THE DRAWINGS

Various aspects of the present disclosure are described hereinbelow with reference to the drawings, which are incorporated in and constitute a part of this specification, wherein.

DETAILED DESCRIPTION

Figure 1:
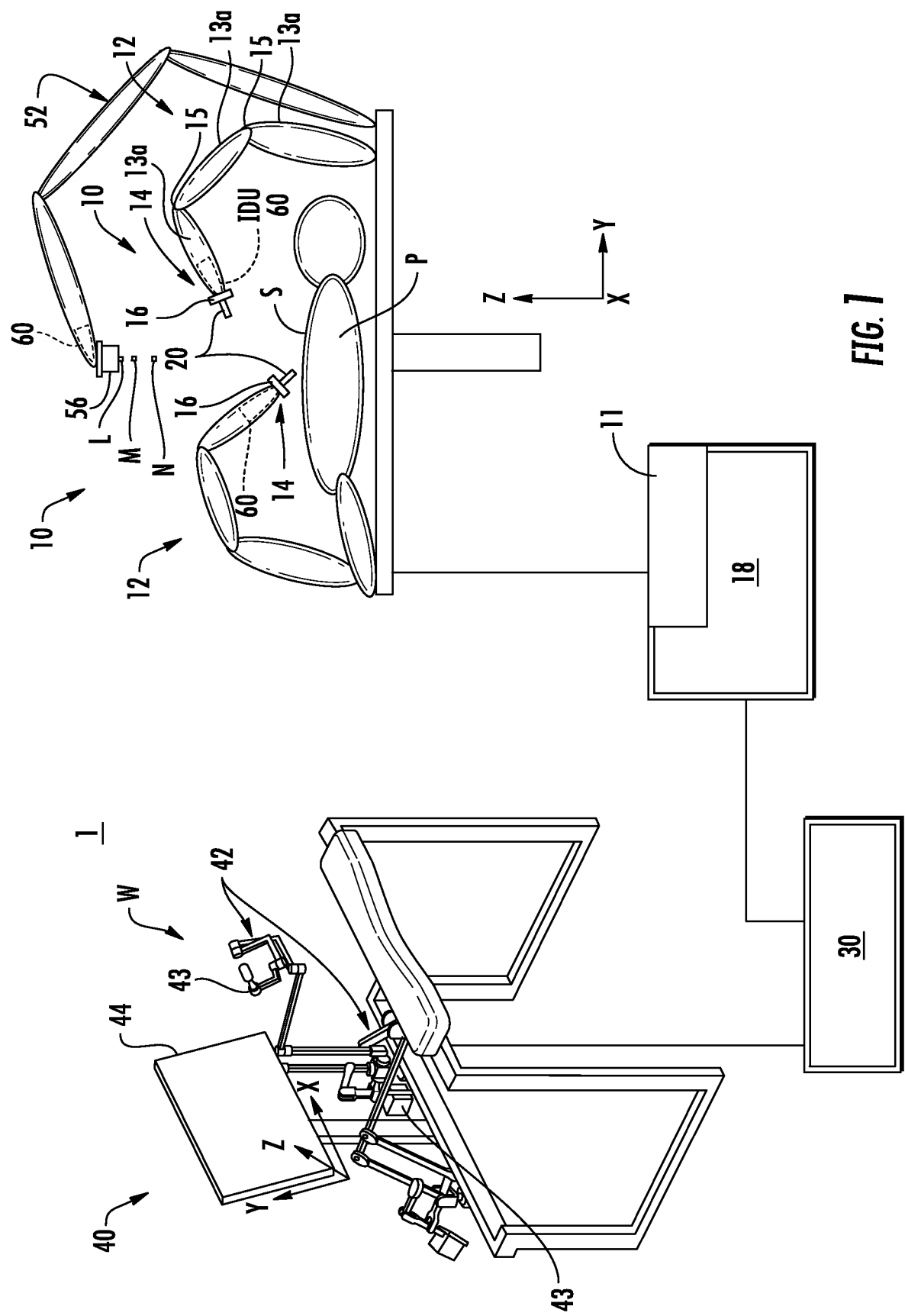
FIG. 1 is a schematic illustration of a robotic surgical system including a robotic surgical assembly in accordance with the present disclosure.

Embodiments of the presently disclosed surgical assembly including a surgical instrument holder, an instrument drive unit (IDU), an adapter assembly, and an endoscope, and methods thereof, are described in detail with reference to the drawings, in which like reference numerals designate identical or corresponding elements in each of the several views. As used herein, the term "clinician" refers to a doctor, a nurse, or any other care provider and may include support personnel. As used herein the term "distal" refers to that portion of the surgical instrument holder, IDU, adapter assembly, and/or endoscope, that is closer to the patient, while the term "proximal" refers to that portion of the surgical instrument holder, IDU, adapter assembly, and/or endoscope, that is farther from the patient.

The present disclosure generally relates to the simplification of determining a torque of a motor from a strain gauge by compensating for manufacturing tolerances and temperature drift of a strain gauge in a measurement circuit outside of a torque or force controller. This disclosure provides a measurement circuit and a method for calibrating the measurement circuit to compensate for manufacturing tolerances and temperature drift. While the disclosed measurement circuit and method are described with respect to a robotic surgical system, the measurement circuit and/or method may be used with a variety of differential sensors that provide readings to controllers and should not limited to robotic surgical systems, strain gauges, and torque readings.

Referring to FIG. 1, a robotic surgical system 1 is shown generally as a robotic system 10, a processing unit 30, and a user interface 40. The robotic system 10 generally includes linkages 12 and a robot base 18. The linkages 12 moveably support an end effector or tool 20 which is configured to act on tissue. The linkages 12 may be in the form of arms each having a plurality of members 13. A member 13a of the plurality of members 13 has an end 14 that supports an end effector or tool 20 which is configured to act on tissue. In addition, the end 14 of the member 13a may include an imaging device 16 for imaging a surgical site "S". Each of the plurality of members 13 of the linkages 12 may be connected to one another about joints 15. The user interface 40 is in communication with the robot base 18 through the processing unit 30. The processing unit 30 may be formed of a single unit or may be distributed to multiple processing units disposed about the robotic surgical system 1. For example, a first processing unit may be associated with the user interface 40 and a second processing unit may be disposed within the robot base 18.

The user interface 40 includes a display device 44 which is configured to display three-dimensional images. The display device 44 displays three-dimensional images of the surgical site "S" which may include data captured by imaging devices 16 positioned on the end 14 of the member 13a and/or include data captured by imaging devices that are positioned about the surgical theater (e.g., an imaging device positioned within the surgical site "5", an imaging device positioned adjacent the patient "P", imaging device 56 positioned at a distal end of an imaging arm 52). The imaging devices (e.g., imaging devices 16, 56) may capture visual images, infra-red images, ultrasound images, X-ray images, thermal images, and/or any other known real-time images of the surgical site "S". The imaging devices transmit captured imaging data to the processing unit 30 which creates three-dimensional images of the surgical site "S" in real-time from the imaging data and transmits the three-dimensional images to the display device 44 for display.

The user interface 40 also includes input handles 42 which allow a clinician to manipulate the robotic system 10 (e.g., move the linkages 12, the ends 14 of the linkages 12, and/or the tools 20). Each of the input handles 42 is in communication with the processing unit 30 to transmit control signals thereto and to receive feedback signals therefrom. Each of the input handles 42 may include input devices which allow the surgeon to manipulate (e.g., clamp, grasp, fire, open, close, rotate, thrust, slice, etc.) the tools 20 supported at the end 14 of the member 13a.

For a detailed discussion of the construction and operation of a robotic surgical system 1, reference may be made to U.S. Pat. No. 8,828,023, entitled "Medical Workstation", the entire contents of which are incorporated herein by reference.

Figure 2:
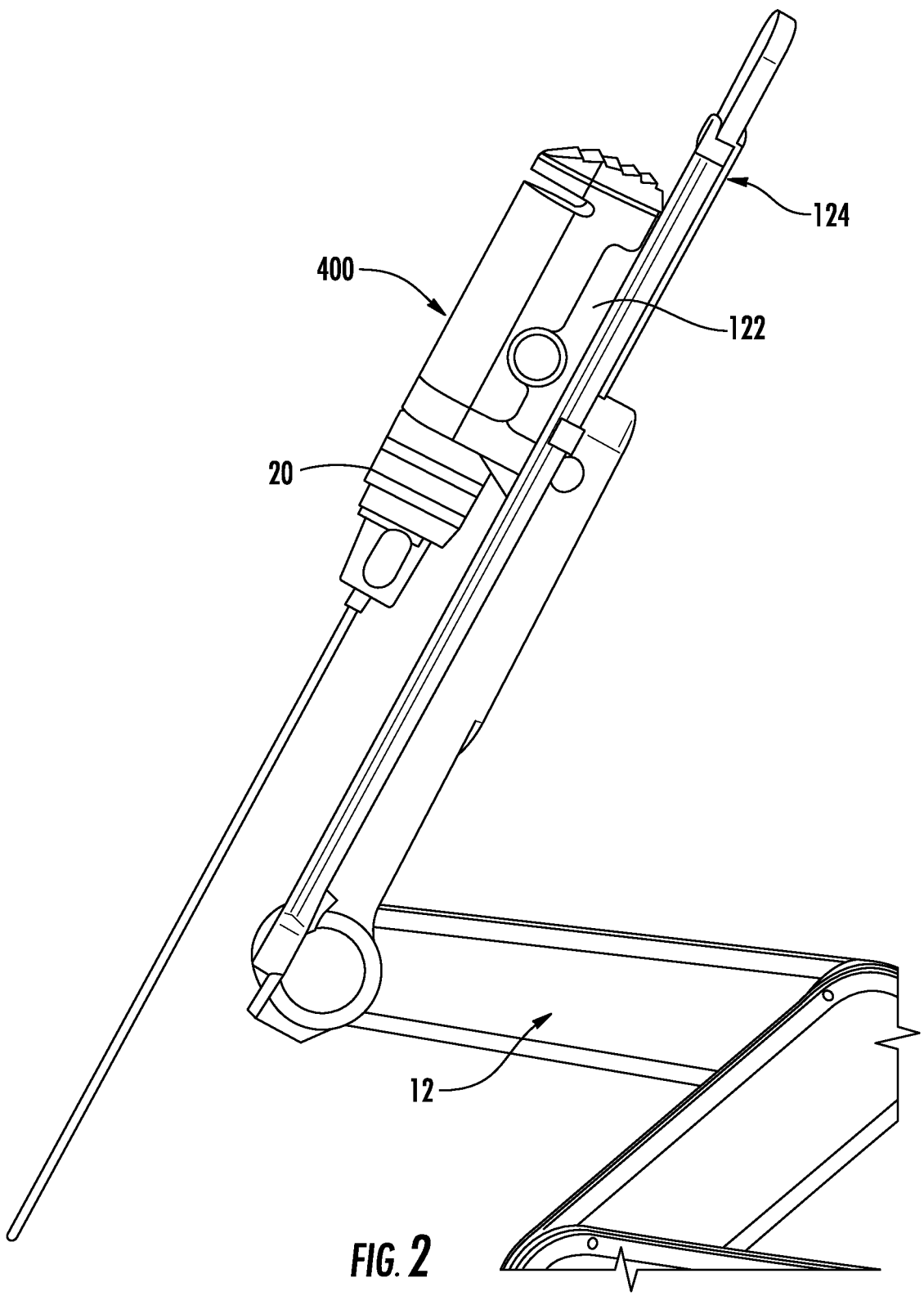
FIG. 2 is a side, perspective view of the surgical assembly of FIG. 1 including a surgical instrument holder, an IDU, an adapter assembly, and a surgical instrument.

With reference to FIG. 2, a portion of an exemplary arm 12 of the surgical robot 10 of FIG. 1. The arm 12 includes a carriage 122 that is translatable along a rail 124. An instrument drive unit (IDU) 400 is secured to the carriage 122. The IDU 400 has a motor assembly 410 (FIG. 3) that is configured to control a tool 20 as detailed below. A brief description of the IDU 400 and motor assembly 410 is provided below. For a detailed discussion of an exemplary IDU including a motor assembly, reference may be made to U.S. Patent Publication No. 2018/0153634, the entire contents of which are incorporated herein by reference.

Figure 3:
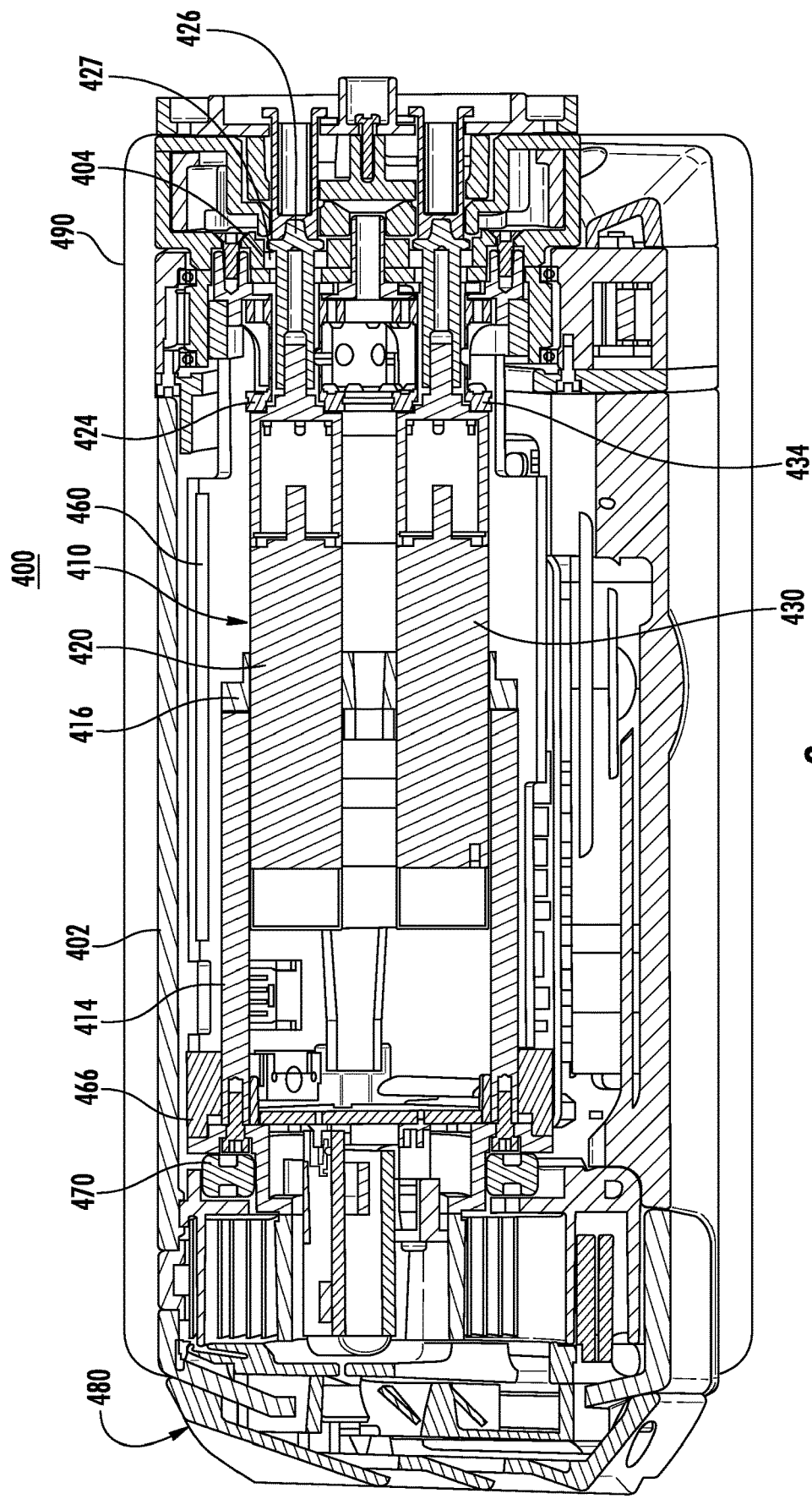
FIG. 3 is a longitudinal cross-sectional view of the instrument drive unit of FIG. 2.

With additional reference to FIG. 3, the motor assembly 410 may include four motors 420, 430 (only two are shown in this view) each having a drive shaft 422, 432 having a non-circular transverse cross-sectional profile (e.g., substantially D-shaped, or the like). In some embodiments, the drive shaft may have a circular transverse cross-sectional profile. The four motors 420, 430 are arranged in a rectangular formation such that respective drive shafts 422, 432 thereof are all parallel to one another and all extending in a common direction. A drive shaft 422 of the motor 420 of motor assembly 410 has a drive coupler, such as, for example, a crown gear 424 configured to operably couple to drive assembly (not explicitly shown) of the tool 20. As motor 420 of motor assembly 410 is actuated, rotation of drive shaft 422 of motor 420 is transferred to the tool 20.

Figure 4:
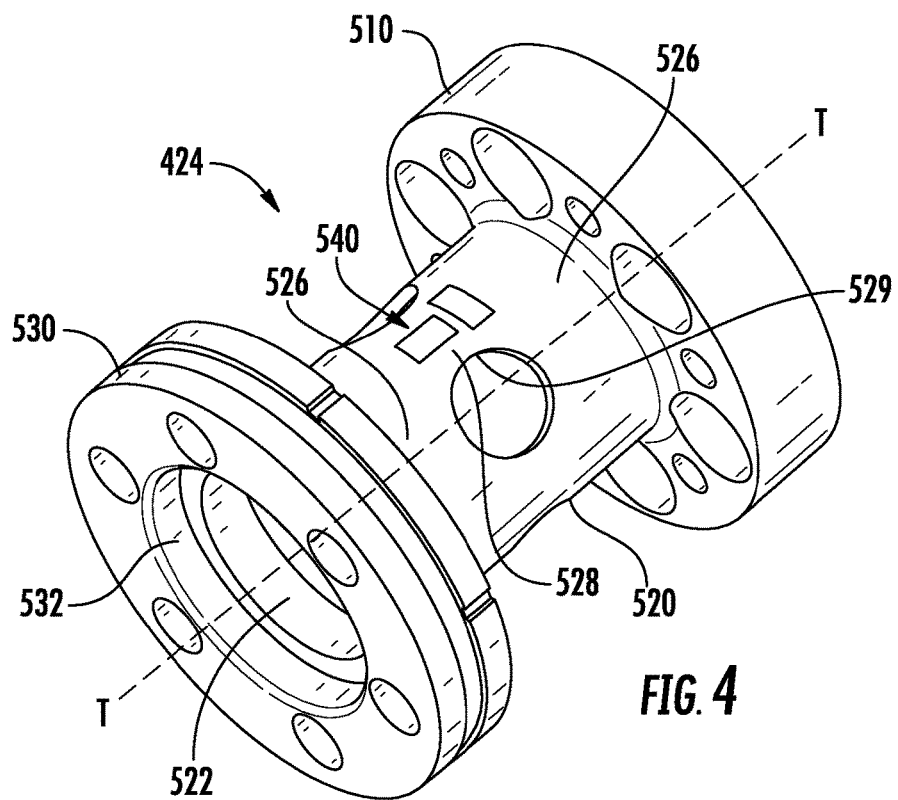
FIG. 4 is a perspective view of a torque transducer of the instrument drive unit of FIG. 3.

Referring also to FIG. 4, the motor 420 is mounted to the torque transducer 424 to secure the motor 420 within the motor assembly 410. It will be appreciated that each of the other motors, e.g., motor 430, is mounted within the motor assembly 410 with a respective torque transducer in a similar manner. The torque transducer 424 is configured as a reaction torque transducer to measure torque of the motor 420 and includes a mounting flange 510, a body 520, and a motor flange 530. The body 520 is generally cylindrical and defines a central longitudinal or transducer axis T-T and defines the channel 522 about the transducer axis T-T. The mounting and motor flanges 510, 530 are constructed to minimize or prevent torsional deflection about the transducer axis T-T. In addition, the mounting flange 510 is secured to the mounting plate 404 by a plurality of fasteners and the motor flange 530 is secured to the distal end portion of the motor 420 to minimize or prevent torsional deflection. The mounting flange 510 and/or the motor flange 530 may be secured to the mounting plate 404 and the motor 420, respectively.

The body 520 is configured to twist or deflect in response to torque of the motor 420. The body 520 can include low strain regions 526 and high strain regions 528 interconnecting the mounting and motor flanges 510, 530. The torque transducer 424 includes a strain gauge 540 disposed on or in the high strain region 528. The strain gauge 540 can be disposed on an inner surface 529a or an outer surface 529b of the high strain region 528 or can be etched into the high strain region 528. The strain gauge 540 is positioned on a portion of the high strain region 528 subject to a maximum flexation or deflection as torque is applied to the torque transducer 424. The strain gauge 540 includes an active strain sensor 542 and a calibration strain sensor 544. The active strain sensor 542 is orientated to measure deflection or flex of the high strain region 528 in response to torque being applied to the torque transducer 424 about the transducer axis T-T as such the active strain sensor 542 measures radial strain of the high strain region 528. The calibration strain sensor 544 is aligned perpendicular to the active strain sensor 542 such that the calibration strain sensor 544 is subject to little or no radial deflection of the high strain region 528 about the transducer axis T-T. The calibration strain sensor 544 measures strain of the high strain region 528 in response to factors other than radial deflection (e.g., thermal expansion of the body 520).

Figure 6:
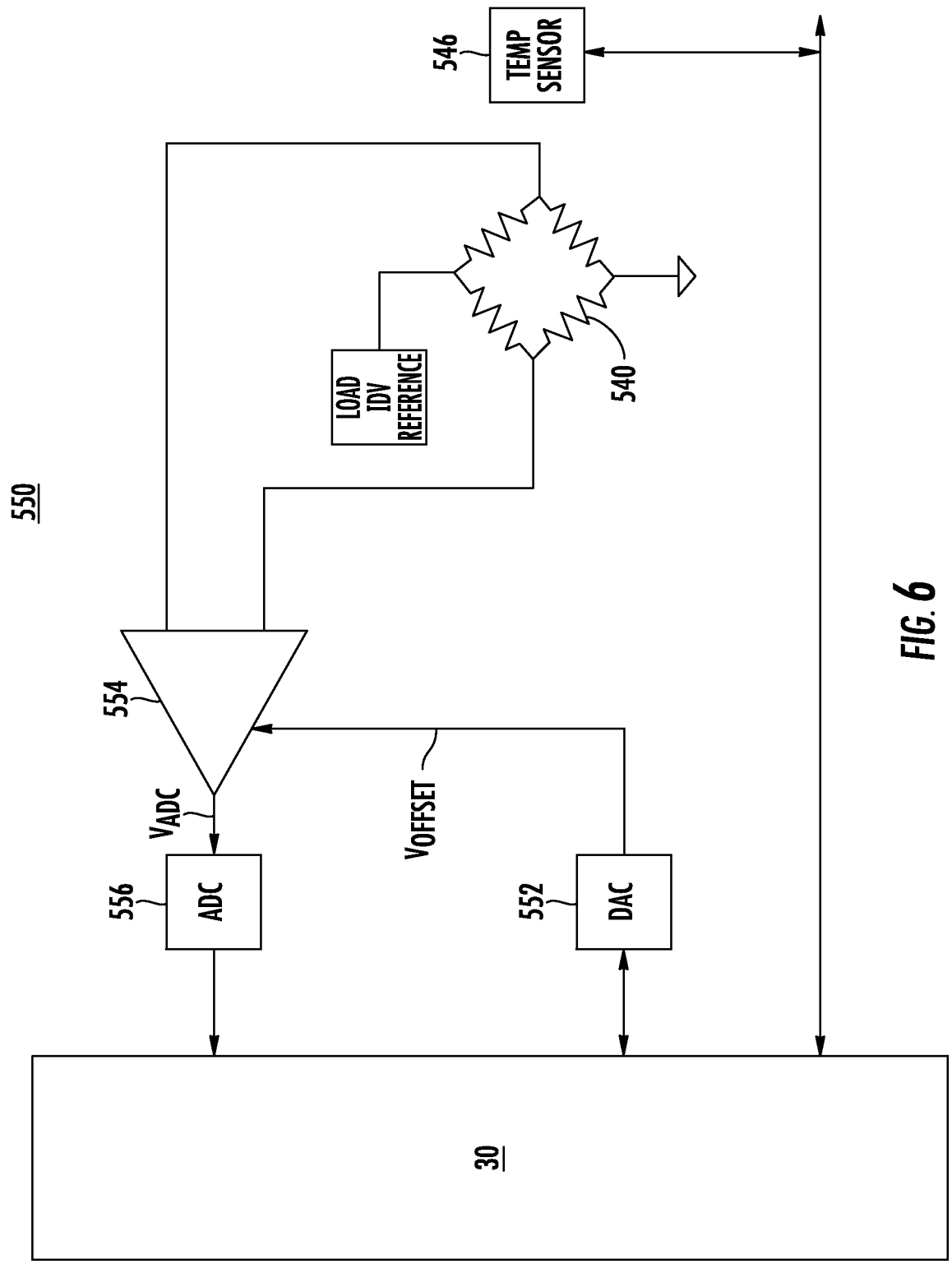
FIG. 6 is a schematic view of a measurement circuit of the IDU of FIG. 2 including the strain gauge of FIG. 5.

The strain gauge 540 measures a load or a torque of the motor 420 by measuring deflection within the torque transducer 424. In response to the torque of the motor 420, the strain gauge 540 provides a differential voltage to a measurement circuit 550 (FIG. 6). The differential voltage provided by the strain gauge 540 may be affected by an operating temperature of the strain gauge 540.

Figure 5:
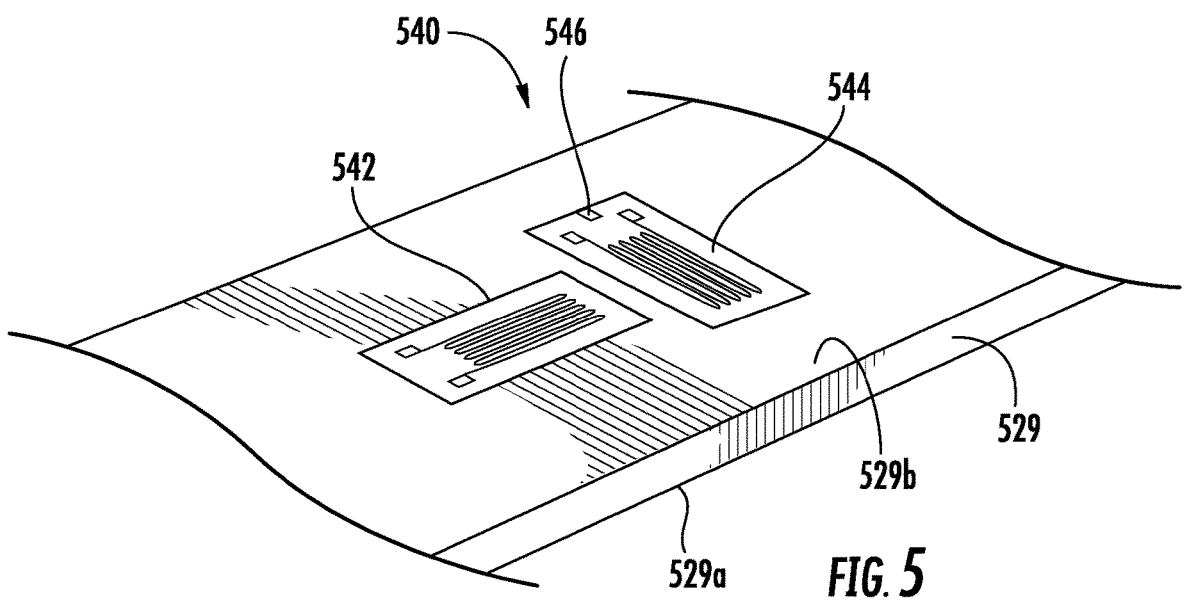
FIG. 5 is an enlarged view of a strain gauge of the torque transducer of FIG. 4.

Referring to FIG. 5, the strain gauge 540 may include an active strain sensor 542 and a calibration strain sensor 544. The calibration strain sensor 544 may compensate for effects of an operating temperature on a gain of the strain gauge 540; however, the differential voltage of provided by the strain gauge 540 may further be effected by an operating temperature of the strain gauge 540 which results in an offset as detailed below.

With additional reference to FIG. 6, the measurement circuit 550 is configured to convert the differential voltage provided by the strain gauge 540 to a digital torque signal for a motion controller, e.g., processing unit 30 (FIG. 1). The measurement circuit 550 is configured to generate a digital torque signal that compensates for the operating temperature and manufacturing tolerances of the strain gauge 540 of the torque transducer 424. The measurement circuit 550 includes the strain gauge 540, a temperature sensor 546, an offset controller or digital-to-analog converter (DAC) 552, an amplifier 554, and an analog-to-digital converter (ADC) 556. In embodiments, the measurement circuit 550 is disposed within the IDU 400 or is disposed within the robot base 18. The temperature sensor 546 provides a temperature signal to the DAC 552 which converts a digital temperature signal to an analog temperature signal and transmits the analog temperature signal to the amplifier 554. The DAC 552, amplifier 554, and/or ADC 556 may be a provided as a system-on-a-chip to provide for real-time sampling and filtering of a differential voltage provided by the strain gauge 540.

The torque sensor 540 measures a load and provides a torque signal to the amplifier 554 in the form of a differential voltage proportional to the load applied to sensor 540. The amplifier 554 uses an offset voltage $V_{OFFSET}$ provided by the DAC 552 as an offset to the torque signal to correct for manufacturing tolerances and temperature drift after applying an analog gain to the offset torque signal as detailed below. The amplifier 554 then transmits an adjusted torque signal or ADC voltage $V_{ADC}$ to the ADC 556 which converts the ADC voltage $V_{ADC}$ from an analog signal to a digital torque signal for use by a motion controller, e.g., processing unit 30. The temperature sensor 546 may provide the digital temperature signal to a DAC, e.g., DAC 552, for strain gauge 540 of the IDU 400 such that a single temperature sensor 546 may be used for the IDU 400. Alternatively, each torque transducer, e.g., torque transducer 424 may have a separate temperature sensor, e.g., temperature sensor 546.

By compensating for temperature drift and manufacturing tolerances of the strain gauge 540 in the measurement circuit 550, compensation for the temperature of the IDU 400, the motor 420, and/or the torque transducer 424 can be removed from a motion controller. Removing temperature compensation from a motion controller may reduce processing time for the motion controller and/or reduce processer load of the motion controller which may result in improved performance of the motion controller. Specifically, this approach does not require any post-processing of the sensor data to correct for temperature/tolerance corrections each time that the sensor, e.g., torque transducer 424 is read. The correction is performed by adjusting the analog signal representing the sensor reading and that because changes due to temperature fluctuations occur at a relatively slow rate, the adjustment due to temperature may be done at a much slower update rate than the rate of reading the differential sensor. Thus, freeing up processor time as well as speeding up the sample delay per cycle.

Figure 7:
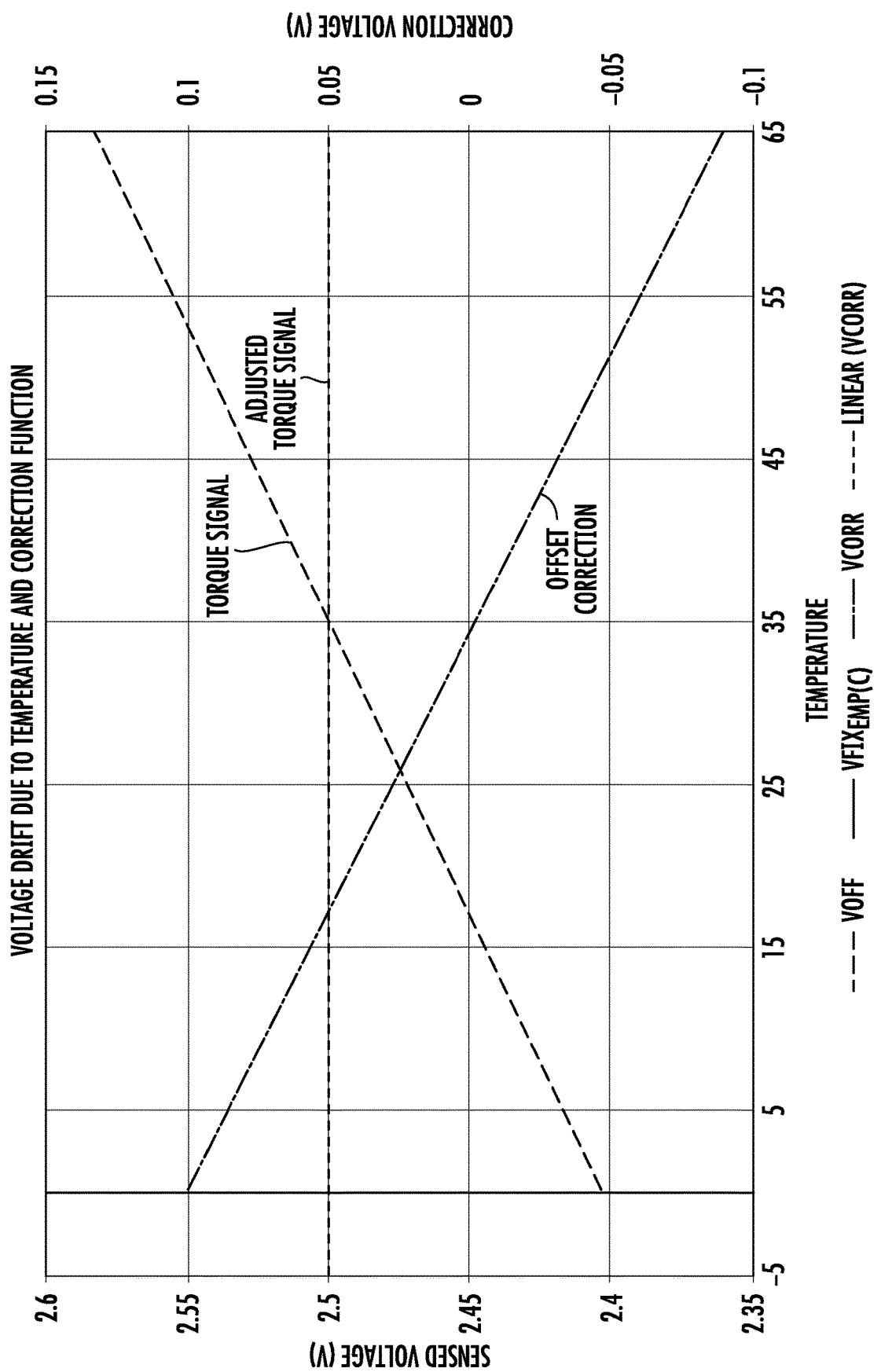
FIG. 7 is graph of an example of voltage drift and offset correction shown as a factor of temperature of the measurement circuit of FIG. 6.

With reference to FIG. 7, a voltage drift of an exemplary strain gauge 540 as a function of temperature in a no-load condition is shown. As shown, voltage of a torque signal provided by the strain gauge 540 increases or decreases in a substantially linear manner as temperature increases. Thus, an offset correction can be developed which, when applied to the torque signal provides a constant adjusted torque signal as shown. The offset correction can be applied to the torque signal by the amplifier 554 after an analog gain is applied to the differential voltage provided by the strain gauge 540. In some embodiments, the voltage of the torque signal provided by the strain gauge 540 varies in a non-linear manner and can be corrected by mapping the corrections to a non-linear function, e.g., quadratic or cubic function.

A mathematical model can be developed to convert torque load of the motor to an adjusted voltage $V_{ADC}$ that is received at the ADC 556 from the amplifier as follows:

$$V_{ADC} = K_{AMP} \cdot V_+ \cdot (V_{SENSOR}(\tau) + V_{OFFSET} + V_{ERR}(T)) + V_{BIAS}(T) \quad (1)$$

where $K_{amp}$ is a gain applied by the amplifier 554, $V_+$ is excitation voltage of the strain gauge 540, $V_{SENSOR}(\tau)$ is the torque signal from the strain gauge 540, $V_{OFFSET}$ is an offset voltage of the strain gauge 540 which is dependent on the excitation voltage $V_+$ and a fixed manufacturing tolerance, $V_{ERR}(T)$ is an error voltage of the strain gauge 540 dependent on temperature as shown in FIG. 7, and $V_{BIAS}(T)$ is a bias voltage applied to the amplifier 554 to correct for the offset and error voltages.

If the offset error and the temperature drift of the strain gauge 540 are ignored, Equation (1) reduces to:

$$V_{ADC} = K_{AMP} \cdot V_+ \cdot (V_{SENSOR}(\tau)) + V_{BIAS} \quad (2)$$

such that the adjusted voltage $V_{ADC}$ is fixed at a midrange input $V_{MID}$, e.g., 2.5 V, with positive torques being above the midrange input and negative torques being below the midrange input.

When the strain gauge 540 is in a no-load state, the conversion function can be shown as:

$$V_{ADC} = K_{AMP} \cdot V_+ \cdot (V_{OFFSET} + V_{ERR}(T)) + V_{BIAS}(T) \quad (3)$$

such that the bias voltage $V_{BIAS}$ regains temperature sensitivity to compensate for the error voltage $V_{ERR}$.

As shown in FIG. 7, the error voltage $V_{ERR}$ can be shown as:

$$V_{ERR}(T) = K_T T + b_T \quad (4)$$

where the constants $K_T$ and $b_T$ can be determined empirically and be verified through testing.

Combining Equations (4) with Equation (3) and fixing the adjusted voltage $V_{ADC}$ to a midrange input of $V_{MID}$, e.g., 2.5 V, provides:

$$V_{MID} = K_{AMP} \cdot V_+ \cdot (K_T T + b_T) + V_{BIAS}(T) \quad (5)$$

which can be rearranged to determine the bias voltage function $V_{BIAS}(T)$ without offset as:

$$V_{BIAS}(T) = V_{MID} - (K_{AMP} \cdot V_+ \cdot K_T) T - (K_{AMP} \cdot V_+ \cdot b_T) \quad (6)$$

Understanding that $K_{AMP}$ and $V_+$ are both constants, these two constants can be combined to yield:

$$V_{BIAS}(T) = V_{MID} - K_T T - b_T \quad (7)$$

In addition, manufacturing tolerances of the strain gauge 540 also introduces a non-temperature sensitive offset to the torque signal that can be compensated for by adjusting the bias voltage $V_{BIAS}(T)$ as follows:

$$V_{MID} = K_{AMP} \cdot V_+ \cdot V_{OFFSET} + V_{BIAS}(T) \quad (8)$$

Again understanding that $K_{AMP}$ and $V_+$ are both constants which can be lumped into the offset voltage $V_{OFFSET}$ providing:

$$V_{OFFSET} = V_{MID} - V_{BIAS}(T) \quad (9)$$

By combining the temperature sensitive and non-temperature sensitive elements provides the bias voltage $V_{BIAS}(T)$ as:

$$V_{BIAS}(T) = V_{MID} - (V_{OFFSET} + (K_T T + b_T)) \quad (10)$$

As the bias voltage $V_{BIAS}(T)$ function is defined, Equation (2) can be used to remove offsets due to manufacturing tolerances and temperature drift such that the zero load voltage at the ADC 556 is the midrange input $V_{MID}$, e.g., 2.5V, in the no load condition across a range of temperatures. By removing manufacturing tolerances and temperature drift from the voltage at the ADC 556, converting the voltage at the ADC 556 to a torque of the system $\tau_{SYSTEM}(V)$ can be reduced to removing the midrange input $V_{MID}$ from the ADC voltage $V_{ADC}$ and multiplying by a gain constant $K_{\tau\_SYSTEM}$ shown as:

$$\tau_{SYSTEM}(V) = K_{\tau\_SYSTEM}(V_{ADC} - V_{MID}) \quad (11)$$

The gain constant $K_{\tau\_SYSTEM}$ can be determined by applying two fixed loads, e.g., torques, to the system. This can be achieved by putting the system in a no-load condition and adjusting the bias of the DAC 552 such that the ADC voltage $V_{ADC}$ is the midrange input value $V_{MID}$, e.g., 2.5V. Then, known positive and negative torques can be applied to the strain gauge 540 and the ADC voltage $V_{ADC}$ is read under each load to calculate the gain constant $K_{\tau\_SYSTEM}$ by:

$$K_{\tau\_SYSTEM} = \frac{\tau_+ - \tau_-}{V_{ADC_{\tau+}} - V_{ADC_{\tau-}}} \quad (12)$$

Figure 8:
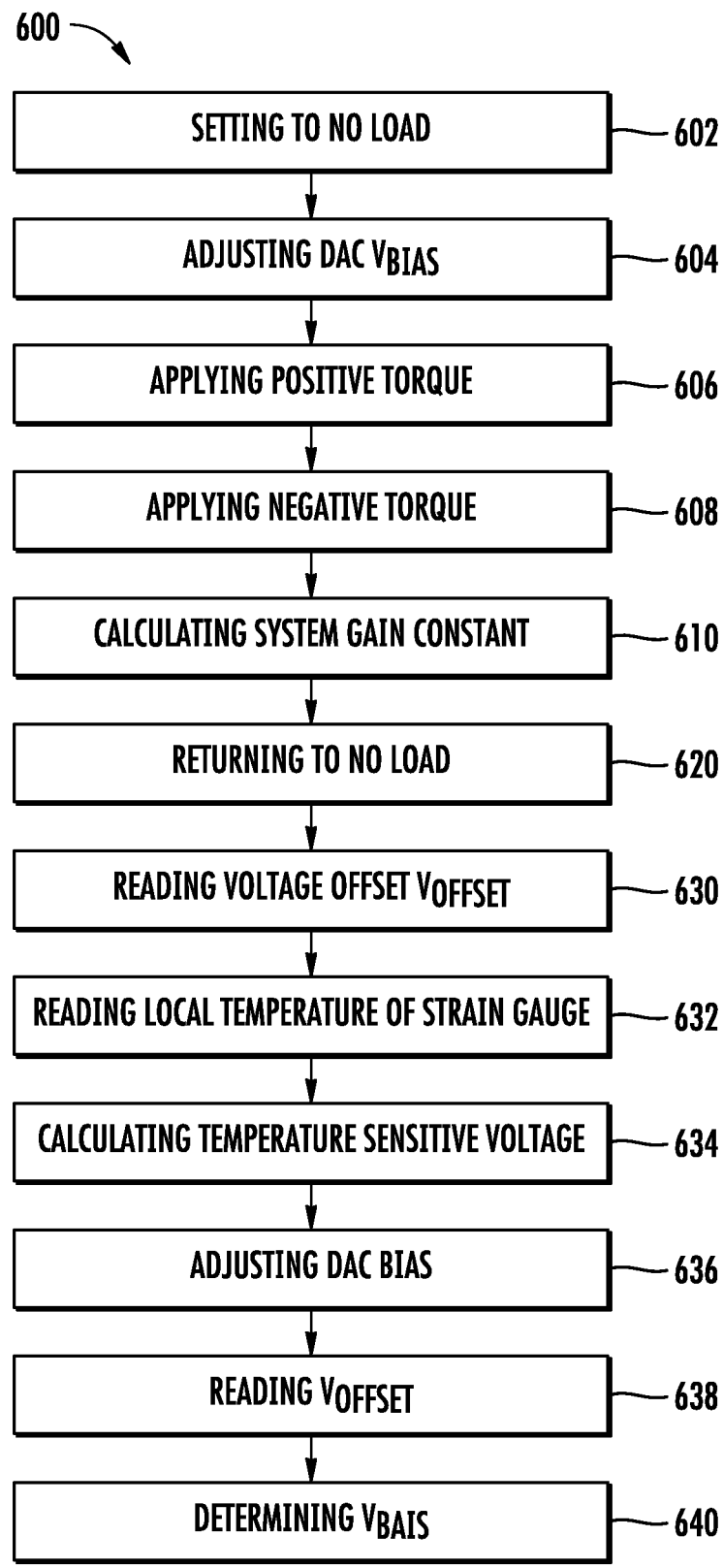
FIG. 8 is a flow chart of a method of calibrating the measurement circuit of FIG. 6.

Referring to FIG. 8, a method 600 of determining a gain constant $K_{\tau\_SYSTEM}$, a voltage bias $V_{BIAS}(T)$, and a voltage offset $V_{OFFSET}$ is disclosed in accordance with the present disclosure with reference to the strain gauge 540 and the measurement circuit 550 of FIG. 6. Initially, the strain gauge 540 is placed in a no load condition (Step 602). With the strain gauge 540 in the no load condition, the voltage bias $V_{BIAS}$ of the DAC 552 is adjusted such that an ADC voltage $V_{ADC}$ outputted by the amplifier 554 is a predetermined midrange value $V_{MID}$, e.g., 2.5V, (Step 604). With the voltage bias $V_{BIAS}$ of the DAC 552 adjusted, a known positive torque $\tau_+$ is applied to the axis of the strain gauge 540 and the ADC voltage is recorded as $V_{ADC\tau+}$ (Step 606) and then a known negative torque $\tau_-$ is applied to the axis of the strain gauge 540 and the ADC voltage is recorded as $V_{ADC\tau-}$ (Step 608). The ratio of the known positive and negative torques $\tau_+$, $\tau_-$ and the recorded ADC voltages $V_{ADC+}$, $V_{ADC-}$ are used in Equation (12) to calculate the gain constant of the system $K_{\tau\_SYSTEM}$ (Step 610).

With the gain constant of the system $K_{\tau\_SYSTEM}$ calculated, the strain gauge 540 is returned to the no load condition (Step 620) to calculate the voltage bias $V_{BIAS}$ to correct for the no load voltage value of the ADC voltage $V_{ADC}$. When calculated, the voltage bias $V_{BIAS}$ includes a first component, e.g., the offset voltage $V_{OFFSET}$, which corrects for manufacturing tolerances which are not temperature dependent and a second component which corrects for temperature drift of the strain gauge 540. By correcting the no load voltage value of the ADC voltage $V_{ADC}$, gain measurements may be reduced to a multiplicative calculation.

First, the offset voltage $V_{OFFSET}$ of Equation (10) is determined (Step 630). To calculate the offset voltage $V_{OFFSET}$, while under no load, the temperature of the strain gauge 540 is determined (Step 632). The local temperature of the strain gauge 540 is then used in Equation (7) to calculate a temperature sensitive voltage which can be used as a value of the bias voltage $V_{BIAS}$ (Step 634). It will be appreciated that the constants for Equation (7) are empirically provided as detailed above. The DAC 552 is then adjusted to the calculated bias voltage $V_{BIAS}$ (Step 636) and the ADC voltage $V_{ADC}$ is read and stored as the offset voltage $V_{OFFSET}$ (Step 638).

With the $V_{OFFSET}$ determined, the temperature compensation of the bias voltage $V_{BIAS}$ can be determined by periodically reading the local temperature of the strain gauge 540 and using the constants and the offset voltage $V_{OFFSET}$ in Equation (10) to calculate the bias voltage $V_{BIAS}$ for a given temperature (Step 640) with the strain gauge 540 in a no load condition. These values are then recorded or written into the non-volatile memory and used by the DAC 552 to offset or bias the amplifier 554 as a function of a temperature of the temperature sensor 546. As temperature effects on the system tend to track at a low rate, the offset of the amplifier 554 may be adjusted at a low rate, e.g., about 1 Hz. These values may be updated at anytime that the strain gauge 540 is in a no load configuration which may allow for removing error due to higher order error terms not detailed herein. A bias voltage $V_{BIAS}(T)$ function may be developed from the recorded values to extrapolate known temperature drift under no load to loaded conditions where there is not a recorded value for the sensed temperature. It will be appreciated that the determining of the bias voltage $V_{BIAS}(T)$ function may occur before, after, or during the calculation of the gain constant of the system $K_{\tau\_SYSTEM}$.

Once the DAC 552 is set to offset the amplifier 554 with the bias voltage $V_{BIAS}(T)$ function and the gain constant of the system $K_{\tau\_SYSTEM}$ is calculated, the torque of the motor associated with the strain gauge 540 can be calculated as:

$$\tau(V) = K_{\tau SYSTEM} \cdot (V_{ADC} - 2.5) \quad (13)$$

By compensating for temperature and manufacturing tolerances in the DAC 552, the calculation of torque is simplified to multiplying the measured ADC voltage $V_{ADC}$ minus the midrange value $V_{MID}$ by the gain constant of the system $K_{\tau\_SYSTEM}$. This greatly simplifies the calculation of torque for a motion controller and thus, may increase the positional accuracy of the surgical robot 10 (FIG. 1) during a surgical procedure.

The systems and/or methods described herein may utilize one or more controllers to receive various information and transform the received information to generate an output. The controller may include any type of computing device, computational circuit, or any type of processor or processing circuit capable of executing a series of instructions that are stored in a memory. The controller may include multiple processors and/or multicore central processing units (CPUs) and may include any type of processor, such as a microprocessor, digital signal processor, microcontroller, programmable logic device (PLD), field programmable gate array (FPGA), or the like. The controller may also include a memory to store data and/or instructions that, when executed by the one or more processors, causes the one or more processors to perform one or more methods and/or algorithms. In example embodiments that employ a combination of multiple controllers and/or multiple memories, each function of the systems and/or methods described herein can be allocated to and executed by any combination of the controllers and memories.

Any of the herein described methods, programs, algorithms or codes may be converted to, or expressed in, a programming language or computer program. The terms "programming language" and "computer program," as used herein, each include any language used to specify instructions to a computer, and include (but is not limited to) the following languages and their derivatives: Assembler, Basic, Batch files, BCPL, C, C+, C++, Delphi, Fortran, Java, JavaScript, machine code, operating system command languages, Pascal, Perl, PL1, scripting languages, Visual Basic, metalanguages which themselves specify programs, and all first, second, third, fourth, fifth, or further generation computer languages. Also included are database and other data schemas, and any other meta-languages. No distinction is made between languages which are interpreted, compiled, or use both compiled and interpreted approaches. No distinction is made between compiled and source versions of a program. Thus, reference to a program, where the programming language could exist in more than one state (such as source, compiled, object, or linked) is a reference to any and all such states. Reference to a program may encompass the actual instructions and/or the intent of those instructions.

Any of the herein described methods, programs, algorithms or codes may be contained on one or more non transitory computer readable or machine-readable media or memory. The term "memory" may include a mechanism that provides (in an example, stores and/or transmits) information in a form readable by a machine such a processor, computer, or a digital processing device. For example, a memory may include a read only memory (ROM), random access memory (RAM), magnetic disk storage media, optical storage media, flash memory devices, or any other volatile or non-volatile memory storage device. Code or instructions contained thereon can be represented by carrier wave signals, infrared signals, digital signals, and by other like signals.

While several embodiments of the disclosure have been shown in the drawings, it is not intended that the disclosure be limited thereto, as it is intended that the disclosure be as broad in scope as the art will allow and that the specification be read likewise. Any combination of the above embodiments is also envisioned and is within the scope of the appended claims. Therefore, the above description should not be construed as limiting, but merely as exemplifications of particular embodiments. Those skilled in the art will envision other modifications within the scope of the claims appended hereto.

What is claimed is:

1. A measurement circuit configured to provide a torque reading to a motion controller, the measurement circuit comprising:
   an offset controller configured to read a temperature signal and to generate an offset voltage in response to reading the temperature signal;
   an amplifier configured to read a differential voltage from a differential sensor and to receive the offset voltage from the offset controller, to add the offset voltage to the differential voltage after applying an analog gain to the differential voltage to generate an adjusted voltage, and to transmit the adjusted voltage; and
   a temperature sensor configured to transmit the temperature signal indicative of a temperature of the differential sensor, wherein the temperature sensor is configured to output the temperature signal as a digital temperature signal and the offset controller is a digital-to-analog converter configured to convert the digital temperature signal to an analog voltage offset indicative of a temperature of the differential sensor.

2. The measurement circuit according to claim 1, wherein the differential sensor is a strain gauge.

3. A measurement circuit configured to provide a torque reading to a motion controller, the measurement circuit comprising:
   an offset controller configured to read a temperature signal and to generate an offset voltage in response to reading the temperature signal;
   an amplifier configured to read a differential voltage from a differential sensor and to receive the offset voltage from the offset controller, to add the offset voltage to the differential voltage after applying an analog gain to the differential voltage to generate an adjusted voltage, and to transmit the adjusted voltage; and
   a differential sensor configured to generate the differential voltage indicative of a torque of a motor and to transmit the differential voltage to the amplifier.

4. The measurement circuit according to claim 3, wherein the offset controller is configured to generate the offset voltage which includes a first component that corrects for manufacturing tolerances of the strain gauge and a second component that corrects for temperature drift of the differential sensor.

5. A measurement circuit configured to provide a torque reading to a motion controller, the measurement circuit comprising:
   an offset controller configured to read a temperature signal and to generate an offset voltage in response to reading the temperature signal;
   an amplifier configured to read a differential voltage from a differential sensor and to receive the offset voltage from the offset controller, to add the offset voltage to the differential voltage after applying an analog gain to the differential voltage to generate an adjusted voltage, and to transmit the adjusted voltage; and
   an analog-to-digital converter configured to receive the adjusted voltage from the amplifier, to convert the adjusted voltage to a digital torque signal indicative of the adjusted voltage which is corrected for temperature drift, and to transmit the torque signal.

6. An instrument drive unit configured to control a tool of a surgical instrument, the instrument drive unit comprising:
   a first motor;
   a first torque transducer including a first torque measurement circuit configured to determine a torque of the first motor, the first torque measurement circuit including:
      an offset controller configured to read a first temperature signal and to generate an offset voltage in response to reading the first temperature signal;
      an amplifier configured to read a differential voltage from a differential sensor, to receive the offset voltage from the offset controller, to add the offset voltage to the differential voltage after applying a gain to the differential voltage to generate an adjusted voltage, and to transmit the adjusted voltage; and an analog-to-digital converter configured to receive the adjusted voltage from the amplifier and to transmit the first torque signal to the motion controller; and a motion controller configured to receive a first torque signal from the first measurement circuit indicative of the adjusted voltage and to control the first motor in response to the first torque signal.

7. The instrument drive unit according to claim 6, further comprising:

a second motor; and a second torque transducer including a second torque measurement circuit configured to determine a torque of the second motor, the motion controller configured to receive a second torque signal from the second measurement circuit indicative of the torque of the second motor which is adjusted for a temperature of the second torque transducer.

8. The instrument drive unit according to claim 7, wherein the first measurement circuit includes a first temperature sensor configured to transmit the first temperature signal indicative of a temperature of the first torque transducer to the offset controller and the second measurement circuit includes a second temperature sensor configured to transmit the second temperature signal indicative of a temperature of the second torque transducer to the offset controller.

9. The instrument drive unit according to claim 7, further comprising a temperature sensor configured to transmit the first temperature signal indicative of a temperature of the first torque transducer to the offset controller and to transmit the second temperature signal indicative of a temperature of the second torque transducer to the offset controller.

10. A method of calibrating a measurement circuit of a differential sensor, the method comprising:

setting a gain constant for the measurement circuit;

determining a bias voltage function of the measurement circuit to compensate for manufacturing tolerances and temperature drift of the differential sensor including:

determining a first component of the bias voltage function of the measurement circuit which is independent of a temperature of the differential sensor;

determining temperature dependent function for a second component of the bias voltage function of the measurement circuit; and generating the bias voltage function from the first and second components of the bias voltage function; and programming the bias voltage function into an offset controller of the measurement circuit, the offset controller configured to receive a temperature signal from a temperature sensor and to generate a bias voltage from the bias voltage function in response to receiving the temperature signal.

11. The method according to claim 10, wherein determining the first component of the bias voltage function includes:

setting the differential sensor in a no load condition;

determining a temperature of the differential sensor;

calculating the second component based on the temperature of the differential sensor;

adjusting the bias voltage of the offset controller of the measurement circuit to the calculated second component;

reading an output voltage of the measurement circuit when the bias voltage is set to the calculated second component; and determining the first component as the difference between a predetermined midrange value and the output voltage of the measurement circuit.

12. The method according to claim 10, wherein determining the second component of the bias voltage function includes:

setting the differential sensor in a no load condition;

adjusting the bias voltage of the offset controller to the first component of the bias voltage function;

recording an output voltage of the measurement circuit and a temperature of the differential sensor at which the output voltage was taken for a plurality of temperatures of the differential sensor in the no load condition; and determining the temperature based function for the second component based on the recorded output voltages.

13. The method according to claim 10, wherein setting the gain constant for the measurement circuit occurs after programming the bias voltage function.

14. The method according to claim 10, wherein setting the gain constant for the measurement circuit includes:

applying a known positive torque to the differential sensor and recording a positive output voltage in response to applying the known positive torque;

applying a known negative torque to the differential sensor and recording a negative output voltage in response to applying the known negative torque; and determining the gain constant of the measurement circuit from a ratio of the known positive and negative torques and the recorded positive and negative output voltages.

15. The method according to claim 14, wherein setting the gain constant for the measurement circuit includes:

setting the differential sensor in a no load condition; and adjusting the bias voltage such that an adjusted voltage of the measurement circuit is a predetermined midrange value before applying the known positive and negative torques.

16. The method according to claim 10, further comprising detecting a no load condition of the differential sensor and updating the bias voltage function based on an output voltage of the measurement circuit and a temperature of the differential sensor when the no load condition is detected.

* * * * *